United States Patent [19]

Henning et al.

[11] Patent Number: 4,912,127
[45] Date of Patent: Mar. 27, 1990

[54] NEW 2-ACYLPYRROLIDINE DERIVATIVES, A PROCESS FOR THE PREPARATION THEREOF, AGENTS CONTAINING THEM, AND THEIR USE

[75] Inventors: Rainer Henning, Hattersheim am Main; Franz Hock, Dieburg; Hansjörj Urbach, Kronberg, all of Fed. Rep. of Germany

[73] Assignee: Hoechst Aktiengesellschaft, Frankfurt am Main, Fed. Rep. of Germany

[21] Appl. No.: 179,292

[22] Filed: Apr. 8, 1988

[30] Foreign Application Priority Data

Apr. 11, 1987 [DE] Fed. Rep. of Germany ....... 3712365

[51] Int. Cl.$^4$ ............... C07D 207/09; C07D 207/12; A61K 31/40
[52] U.S. Cl. .................................. 514/422; 530/330; 530/331; 548/518; 548/526; 548/527; 548/540; 548/536; 548/538
[58] Field of Search ............... 260/998.2; 530/331; 548/518, 530, 531, 532, 533, 535, 536, 537, 538, 540; 514/422

[56] References Cited

U.S. PATENT DOCUMENTS

| | | | |
|---|---|---|---|
| 4,077,951 | 3/1978 | Loffet | 548/518 |
| 4,277,395 | 7/1981 | Bey et al. | 548/537 X |
| 4,439,619 | 3/1984 | Bey et al. | 260/998.2 X |
| 4,456,594 | 6/1984 | Pfeiffer | 548/518 X |
| 4,483,991 | 11/1984 | Freed | 548/518 X |
| 4,499,102 | 2/1985 | Oya et al. | 548/533 X |
| 4,518,528 | 5/1985 | Rasnick | 548/533 |
| 4,560,795 | 12/1985 | Bey et al. | 260/998.2 X |
| 4,719,200 | 1/1988 | Eguchi et al. | 530/331 X |
| 4,720,554 | 1/1988 | Irie et al. | 548/533 |
| 4,762,821 | 8/1988 | Nestor | 548/538 X |

FOREIGN PATENT DOCUMENTS 0268281  5/1988  European Pat. Off. ............ 548/518

*Primary Examiner*—Joseph Paul Brust
*Attorney, Agent, or Firm*—Finnegan, Henderson, Farabow, Garrett and Dunner

[57] ABSTRACT

The invention rleates to pyrrolidine derivatives of the general formula

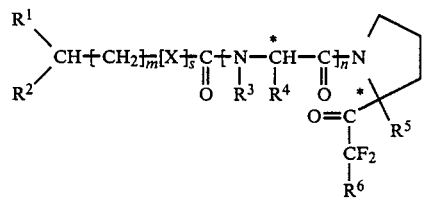

in which $R^1$, $R^2$, $R^3$, $R^4$, $R^5$ and $R^6$ have the meaning indicated in the description; X denotes oxygen, imino or N-alkylimino; m is 0–5; n is 0–2 and s is 0 or 1; a process for their preparation, agents containing them, and their use.

11 Claims, No Drawings

NEW 2-ACYLPYRROLIDINE DERIVATIVES, A PROCESS FOR THE PREPARATION THEREOF, AGENTS CONTAINING THEM, AND THEIR USE

The invention relates to pyrrolidine derivatives of the general formula I

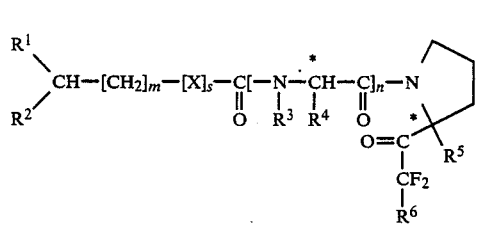

in which $R^1$ denotes hydrogen; $(C_1-C_6)$-alkyl or $(C_6-C_{12})$-aryl which is optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino or a $(C_1$ or $C_2)$-alkylenedioxy;

$R^2$ denotes hydrogen; $(C_1-C_6)$-alkyl; $(C_6-C_{12})$-aryl; $(C_6-C_{12})$-aryloxy; $(C_7-C_{13})$-aroyl; hydroxyl or $(C_1-C_4)$-alkoxy, each of aryl, aryloxy and aroyl being optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one $(C_1$ or $C_2)$-alkylenedioxy; or $R^1$ and $R^2$ together represent benzylidene in which the phenyl ring is optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one $(C_1$ or $C_2)$-alkylenedioxy;

$R^3$ denotes hydrogen; $(C_1-C_6)$-alkyl; $(C_6-C_{12})$-aryl-$(C_1-C_6)$-alkyl; $(C_5-C_9)$-cycloalkyl; indanyl or tetrahydronaphthyl;

$R^4$ denotes hydrogen; $(C_1-C_6)$-alkyl which can be monosubstituted by amino, $(C_1-C_6)$-acylamino, in particular $(C_1-C_6)$-alkanoylamino or Boc-NH, or benzoylamino; $(C_2-C_6)$-alkenyl; $(C_5-C_9)$-cycloalkyl; $(C_5-C_9)$-cycloalkenyl; $(C_5-C_7)$-cycloalkyl-$(C_1-C_4)$-alkyl; $(C_6-C_{12})$-aryl or partially hydrogenated $(C_6-C_{12})$-aryl, each of which can be substituted by one, two or three identical or different radicals from the series comprising $(C_1-C_4)$-alkyl, $(C_1$ or $C_2)$-alkoxy and halogen; $(C_6-C_{12})$-aryl-$(C_1-C_4)$-alkyl or $(C_7-C_{13})$-aroyl-$(C_1$ or $C_2)$-alkyl, both of which can be substituted as defined above in the aryl radical; a monocyclic or bicyclic heterocyclic radical having 5 to 7 or 8 to 10 ring atoms, 1 to 9 of these ring atoms representing carbon atoms and 1 to 2 of these ring atoms representing sulfur or oxygen atoms and/or 1 to 4 of these ring atoms representing nitrogen atoms; or, if not already comprised by the above definitions, the optionally protected side-chain of a naturally occurring α-amino acid, or $R^3$ and $R^4$ together represent —$[CH_2]_p$— in which p is 3, 4 or 5, and in which one methylene group can be replaced by S or O;

$R^5$ denotes hydrogen; $(C_1-C_6)$-alkyl; $(C_6-C_{12})$-aryl-$(C_1-C_5)$-alkyl which is optionally substituted in the aryl moiety by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one $(C_1$ or $C_2)$-alkylenedioxy;

$R^6$ denotes $(C_1-C_8)$-alkyl; $(C_4-C_{10})$-cycloalkyl or $(C_4-C_{10})$-cycloalkyl-$(C_1-C_4)$-alkyl, it being possible for one cycloalkyl radical also to contain, dependent on the ring size, up to 4 double-bonds, and/or to be bridged up to three times; $(C_6-C_{12})$-aryl-$(C_1-C_5)$-alkyl which is optionally substituted in the aryl moiety by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one $(C_1$ or $C_2)$-alkylenedioxy; fluorine or a radical $C_qH_{(2q+1-r)}F_r$ with $q=1, 2, 3, 4$ or $5$ and $r=$ an integer from 1 to $(2q+1)$;

X denotes oxygen; imino or N-$(C_1-C_8)$-alkylimino;

m is 0, 1, 2, 3, 4 or 5;

n is 0, 1 or 2, and s is 0 or 1;

and to their physiologically tolerated salts if such can be formed.

Alkyl can be straight-chain or branched and is, for example, methyl, ethyl, propyl, isopropyl, butyl, isobutyl, sec.-butyl, tert.-butyl, pentyl, isopentyl, neopentyl, sec.-pentyl, tert.-pentyl, hexyl, isohexyl, heptyl or octyl. Corresponding statements apply to radicals derived therefrom, such as alkoxy, alkylamino, dialkylamino, alkanoyl, alkoxycarbonyl and aralkyl.

Aryl is, for example, phenyl, α- or β-naphthyl, or 2-, 3- or 4-biphenylyl; phenyl is preferred. Corresponding statements apply to radicals derived therefrom, such as aryloxy, aralkyl, aryl, aroyl and arylalkanoyl.

Halogen is fluorine, chlorine, bromine or iodine; fluorine, chlorine and bromine are preferred.

Examples of definitions of $R^4$ in the meaning of a monocyclic or bicyclic heterocyclic radical having 5 to 7 or 8 to 10 ring atoms, 1 to 9 of these ring atoms representing carbon atoms and 1 to 2 of these ring atoms representing sulfur or oxygen atoms and/or 1 to 4 of these ring atoms representing nitrogen atoms, are thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Compounds of the formula I have chiral carbon atoms. The invention relates to both the R and the S configurations at all centers of asymmetry. Thus the compounds of the formula I can exist as optical isomers, as diasteromers, as racemates or as mixtures thereof. However, the compounds of the formula I which are preferred are those in which the carbon atoms labeled with an asterisk (*) have the S configuration. Where $R^4$ represents the side-chain of cysteine, however, the R configuration of this center is preferred.

Naturally occurring α-amino acids such as, for example, Ala, Val, Leu, Ile, Phe, Abu, C-Ph-Gly, His, Trp, Lys, Orn, Dab, Dap, Daap, Dapi, Arg, Cit, Glu, Gln, Asp, Asn, Cys, Met, Hyl, Ser, Thr and Tyr are described in, for example, Ann. Rev. Biochem. 38 [1969] 137–158 and FEBS Letters 64 [1976] 29–35.

Where $R^4$ represents a protected side-chain of a naturally occurring α-amino acid such as, for example, protected Ser, Thr, Asp, Asn, Glu, Gln, Arg, Lys, Hyl, Cys, Orn, Cit, Tyr, Trp or His, the protective groups which are preferred are those customary in peptide chemistry (cf., for example, T. W. Greene, "Protective Groups in Organic Synthesis, New York, 1981 or Bodanszky, Bodanszky, "Principles and Practice of Peptide Synthesis", Berlin, 1984).

Where $R^4$ denotes a protected lysine side-chain, the known amino protective groups are preferred, but in particular ($C_1$–$C_6$)-alkanoyl. Where $R^4$ denotes a protected tyrosine side-chain the ether protective group on the oxygen is preferred, in particular ($C_1$–$C_6$)-alkyl; particularly preferred protective groups are methyl and ethyl.

Suitable salts are, in particular, alkali metal or alkaline earth metal salts, salts with physiologically tolerated amines, and salts with inorganic or organic acids such as, for example, HCl, HBr, $H_2SO_4$, maleic acid and fumaric acid.

Preferred compounds of the formula I are those in which $R^1$ denotes hydrogen; ($C_1$–$C_4$)-alkyl or phenyl which is optionally substituted by one or two identical or different radicals from the series comprising methyl, ethyl, methoxy, fluorine, chlorine, bromine, nitro, hydroxyl, amino, methylamino and dimethylamino, or three methoxy or one methylenedioxy;

$R^2$ denotes hydrogen; phenyl; phenoxy; benzoyl; hydroxyl or methoxy, each of phenyl, phenoxy and benzoyl optionally being substituted by one or two identical or different radicals from the series comprising methyl, ethyl, methoxy, fluorine, chlorine, bromine, nitro, hydroxyl, amino, methylamino and dimethylamino, or one methylenedioxy; or $R^1$ and $R^2$ together represent benzylidene in which the phenyl radical is optionally substituted by one or two identical or different radicals from the series comprising methyl, ethyl, methoxy, fluorine, chlorine, bromine and hydroxyl, three methoxy or one methylenedioxy;

$R^3$ denotes hydrogen; ($C_1$–$C_4$)-alkyl; benzyl; phenethyl; cyclopentyl; cyclohexyl or indanyl;

$R^4$ denotes hydrogen or the optionally protected side-chain of a naturally occurring α-amino acid; or $R^3$ and $R^4$ together represent a radical —[$CH_2$]$_p$— which is defined as in claim 1 and in which p is 3 or 4;

$R^5$ denotes hydrogen; methyl; ethyl; benzyl or phenethyl; each of which is optionally substituted in the phenyl radical by one, two or three identical or different radicals from the series comprising methoxy, fluorine, chlorine and bromine, or one methylenedioxy;

$R^6$ denotes ($C_1$–$C_8$)-alkyl; ($C_5$–$C_8$)-cycloalkyl; phenyl; benzyl; phenethyl; fluorine or perfluoro-($C_1$–$C_5$)-alkyl, it being possible for phenyl, benzyl and phenethyl to be substituted in the phenyl radical by one, two or three identical or different radicals from the series comprising methyl, ethyl, methoxy, ethoxy, fluorine, chlorine and bromine, or one methylenedioxy;

X denotes oxygen;
m is 0, 1, 2, 3, 4 or 5;
n is 0 or 1, and
s is 0 or 1,
and their physiologically tolerated salts.

Particularly preferred compounds of the formula I are those in which $R^1$ denotes hydrogen; methyl; ethyl; propyl; isopropyl; phenyl; o-, m- or p-tolyl; o-, m- or p-chlorophenyl; o-, m- or p-fluorophenyl; o-, m- or p-methoxyphenyl or 1,3-, 2,4-, 2,5-, 2,6-, 3,4- or 3,5-dimethoxyphenyl;

$R^2$ denotes hydrogen; phenyl; o-, m- or p-tolyl; o-, m- or p-chlorophenyl; o-, m- or p-fluorophenyl; o-, m- or p-methoxyphenyl; 2,3-, 2,4-, 2,5-, 2,6-, 3,4- or 3,5-dimethoxyphenyl; phenoxy; o-, m- or p-tolyloxy; o-, m- or p-chlorophenoxy, o-, m- or p-fluorophenoxy; o-, m- or p-methoxyphenoxy; 2,3-, 2,4-, 2,5-, 2,6-, 3,4- or 3,5-dimethoxyphenoxy; benzoyl; o-, m- or p-toluoyl; o-, m- or p-chlorobenzoyl; o-, m- or p-fluorobenzoyl; o-, m- or p-methoxybenzoyl; 2,3-, 2,4-, 2,5-, 2,6-, 3,4- or 3,5-dimethoxybenzoyl; hydroxyl or methoxy; or $R^1$ and $R^2$ together represent benzylidene; o-, m- or p-methylbenzylidene; o-, m- or p-methoxybenzylidene or 2,3-, 2,4-, 2,5-, 2,6-, 3,4- or 3,5-dimethoxybenzylidene;

$R^3$ denotes hydrogen, methyl or benzyl;

$R^4$ denotes hydrogen; methyl; n-butyl; isopropyl; isobutyl; sec.-butyl or benzyl; or $R^3$ and $R^4$ together represent —$CH_2$]$_3$—;

$R^5$ denotes hydrogen or methyl;

$R^6$ denotes ($C_1$–$C_6$)-alkyl; ($C_5$–$C_8$)-cycloalkyl; phenyl; benzyl; phenethyl; fluorine or perfluoro-($C_1$–$C_5$)-alkyl, it being possible for phenyl, benzyl and phenethyl to be substituted in the phenyl radical by one or two identical or different radicals from the series comprising methyl, methoxy, fluorine and chlorine, three methoxy, or one methylenedioxy;

X denotes oxygen;
m is 0, 1, 2, 3, 4 or 5;
n is 0 or 1, and
s is 0 or 1,
and their physiologically tolerated salts.

Especially preferred compounds of the formula I are those in which $R^2$ denotes hydrogen;
$R^3$ and $R^4$ together represent —[$CH_2$]$_3$—;
$R^5$ denotes hydrogen;
X denotes oxygen;
m is 1, 2, 3 or 4;
n is 1, and
s is 0 or 1,
and those compounds of the formula I in which
$R^5$ denotes hydrogen;
X denotes oxygen;
m is 1, 2, 3 or 4;
n is 0, and
s is 0 or 1.

The invention also relates to a process for the preparation of compounds of the formula I, which comprises (a) oxidizing a compound of the formula IV

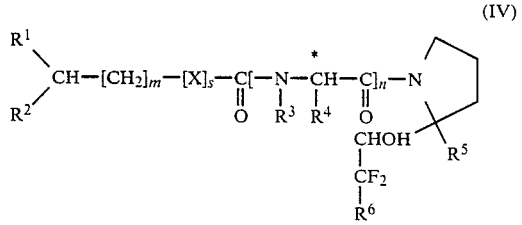

(IV)

in which $R^1$, $R^2$, $R^3$, $R^4$, $R^5$, $R^6$, X, m, n and s have the same meaning as in formula I;

(b) reacting a compound of the formula IX

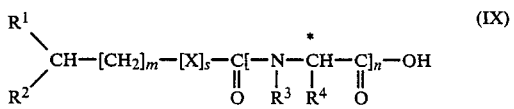

in which $R^1$, $R^2$, $R^3$, $R^4$, X, m, n and s have the same meaning as in formula I with a compound of the formula X

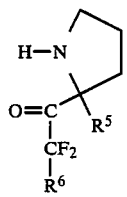

in which $R^5$ and $R^6$ have
the same meaning as in
formula I, and optionally converting the compounds obtained according to (a) or (b) into their physiologically tolerated salts.

The following oxidizing agents are suitable for process variant (a): manganese dioxide, sodium or potassium dichromate, Jones' reagent ($CrO_3$ in aqueous sulfuric acid), N-bromoacetamide, N-bromosuccinimide, dimethyl sulfoxide, Ceric ammonium nitrate, $CrO_3$ in pyridine, tert.-butyl chromate, dipyridine-$CrO_3$, potassium hypochlorite or iodosobenzene. Suitable reaction media are petroleum ether, benzene, carbon tetrachloride or, in the case of $MnO_2$, dilute sulfuric acid. The oxidation is carried out between 0° C. and the boiling point of the reaction mixture.

The preferred oxidizing agent is dimethyl sulfoxide with various additives as described in, for example, Houben-Weyl, volume E3, pages 275–281. Particularly preferred is oxidation with dimethyl sulfoxide in the presence of oxalyl chloride, as well as the process described in J. Org. Chem. 48 [1983] 4155.

Compounds of the formula IV are prepared, for example, by reaction of a compound of the formula II

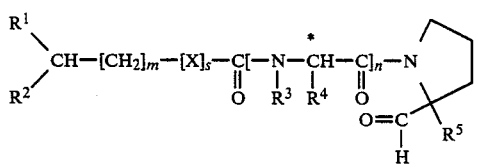

in which $R^1$, $R^2$, $R^3$, $R^4$, $R^5$, X, m, n and s have the same meaning as in formula I, with a compound of the formula III

in which $R^6$ has the same meaning as in formula I, and Y denotes halogen, preferably chlorine, bromine or iodine, in an inert solvent such as an ether or dimethylformamide, with the assistance of a metal such as lithium, sodium, potassium, magnesium or zinc, the latter being preferred, at 0° C. to the boiling point of the solvent, preferably at 20° to 80° C., with or without additional treatment with ultrasound.

The reaction of a compound of the formula IX with a compound of the formula X according to process variant (b) is carried out, for example, in analogy to the amide-coupling processes customary in peptide chemistry, as are described, for example, in Houben-Weyl, Volume 15/2, pages 1–364; in Bodanszky, Bodanszky, "Principles and Practice in Peptide Synthesis", Berlin, 1984, and U.S. Pat. Nos. 4,331,592 and 4,426,325, in an organic solvent such as DMF, $CH_2Cl_2$ or DMA in the presence of coupling auxiliaries such as carbodiimides (for example dicyclohexylcarbodiimide), diphenylphosphoryl azide, alkanephosphoric anhydrides, dialkylphosphinic anhydrides or N,N-succinimidyl carbonates in a solvent such as $CH_3CN$. The compounds of the formula II can be converted into active esters (for example with 1-hydroxybenzotriazole), mixed anhydrides (for example with chloroformic esters), azides or carbodiimide derivatives, and can thus be activated (see Schröder, Lübke, The Peptides, Volume 1, New York 1965, pages 76–136). The reaction is preferably carried out between −20° C. and the boiling point of the reaction mixture.

Compounds of the abovementioned formula II can also be obtained by reacting a compound of the formula V

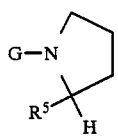

in which $R^5$ has the same meaning as in formula I, and in which G denotes a group which permits the elimination of a hydrogen atom in the α position to the nitrogen atom, in particular a group of the formula

in which $R^9$ denotes ($C_1$-$C_8$)-alkyl, preferably tert-butyl, or ($C_1$-$C_8$)-alkoxy-($C_1$-$C_8$)-alkyl, in an inert solvent such as dialkyl ether or tetrahydrofuran, at −100° C. to 0° C., in particular at −80° C. to −20° C., with a strong base, in particular a ($C_1$-$C_4$)-alkyllithium compound, phenyllithium, a lithium di-($C_1$-$C_4$)-alkylamide or a lithium ($C_5$-$C_6$)-cycloalkyl-($C_1$-$C_4$)-alkylamide, and then with a compound of the formula VI

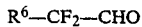

in which $R^6$ has the same meaning as in formula I, resulting in a compound of the formula VII

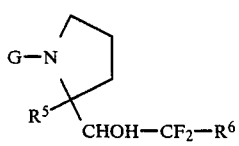

in which G, $R^5$ and $R^6$ are as defined above, eliminating from this the group G in a manner known per se, for example by treatment with an acid or a base, and coupling the resulting compound of the formula VIII

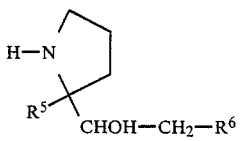

(VIII)

in which $R^5$ and $R^6$ are as defined above, with a compound of the formula IX defined above. The coupling is carried out, for example, in the manner described for process variant (a).

Compounds of the formula II are either known from the literature or can be prepared in analogy to processes known from the literature; some representatives are described, for example, in European Patent Applications EP-A-172,458 and EP-A-201,742 and Japanese Patent Application 1183-297 and in Life Sci. 33, 2149 (1983).

The compounds of the formula I, according to the invention, are inhibitors of prolyl endopeptidase (EC 3.4.21.26). It is known of this enzyme that it degrades neuropeptides such as substance P, neurotensin, LHRH, TRH, vasopressin and angiotensin II (Life Sci. 33, 2149 (1983)). These neuropeptides are associated with important functions in the central nervous system (CNS). Inhibition of their degradation by inhibiting prolyl endopeptidase by compounds of the formula I initiates various effects in the CNS, in particular antiamnestic, antipsychotic, anxiolytic and antidepressant effects.

Hence compounds of the formula I are suitable for the treatment of various disorders of the central nervous system, in particular as nootropics and antipsychotics, in warm-blooded species, preferably in humans. The compounds according to the invention can be administered intravenously, subcutaneously or orally, alone or combined with other substances acting on the CNS.

The dosage depends on the nature and severity of the disorder which is to be treated and is 0.001–20 mg/kg/day, in particular 0.01–10 mg/kg/day. It can also be increased in severe cases, since no toxic properties have hitherto been observed.

The compounds according to the invention can be administered orally or parenterally in appropriate pharmaceutical formulation. For a form for oral administration, the active compounds are mixed with the additives customary for this purpose, such as excipients, stabilizers or inert diluents, and converted by customary methods into suitable presentations such as tablets, coated tablets, hard gelatin capsules, aqueous, alcoholic or oily suspensions or aqueous, alcoholic or oily solutions. Examples of inert excipients which can be used are gum arabic, magnesium carbonate, potassium phosphate, lactose, glucose or starch, especially corn starch. in this connection, preparation can be effected either as dry or wet granules. Examples of suitable oily excipients or solvents are vegetable and animal oils, such as sunflower oil or fish liver oil.

For subcutaneous or intravenous administration, the active compounds or their physiologically tolerated salts are converted into solution, suspension or emulsion, if desired with the substances customary for this purpose, such as solubilizers, emulsifiers or other auxiliaries. Examples of suitable solvents for the new active compounds and the corresponding physiologically tolerated salts are: Water, physiological saline solutions or alcohols; for example ethanol, propanediol or glycerol, as well as sugar solutions such as glucose or mannitol solutions, or a mixture of the various solvents mentioned.

EXAMPLE 1

N-(N-Benzyloxycarbonyl-S-prolyl)-2-S-trifluoroacetylpyrrolidine (a) N-(N-Benzyloxycarbonyl-S-prolyl-2-S-(1-hydroxy-2,2,2-trifluoroethylpyrrolidine 10 g of trifluoroiodomethane are passed into a mixture of 1.65 g of N-benzyloxycarbonyl-S-prolyl-S-prolinal and 0.65 g of zinc powder in 15 ml of dimethylformamide at 20° C., while sonicating in an ultrasound bath. After 5 hours, 100 ml of aqueous 0.1N hydrochloric acid are added, the mixture is extracted with ethyl acetate, and the combined ethyl acetate phases are washed three times with water, dried with MgSO4 and concentrated. Chromatography on silica gel (ethyl acetate/cyclohexane (4:1)) provides 0.6 g of the title compound as oil.

| $^1$H NMR (CDCl$_3$): $\delta$ = | 7.4–7.3 (m, 5H); 5.5–4.9 (m, 2H); 4.7–4.4 (m, 1H); 4.3–4.1 (m, 1H); 4.0–3.2 (m, 5H); 2.4–1.8 (m, 8H) ppm. |
|---|---|

(b) N-(N-Benzyloxycarbonyl-S-prolyl)-2-S-trifluoroacetylpyrrolidine 0.25 ml of dimethyl sulfoxide is added at −78° C. to a solution of 0.15 ml of oxalyl chloride in 20 ml of dichloromethane. After 20 minutes, 0.6 g of the compound from Example (1a) is added, the mixture is stirred for 15 minutes, and then 1.05 ml of triethylamine is added. After a further 5 minutes, the mixture is warmed to room temperature, washed successively with water, aqueous 0.1N hydrochloric acid, aqueous 10% strength Na2CO3 solution and water, dried Na2SO4 and concentrated. Chromatography on silica gel provides 0.395 g of the title compound as oil.

| $^1$H NMR (CDCl$_3$): $\delta$ = | 7.4–7.2 (m, 5H); 5.25–4.9 (m, 3H); 4.7–4.1 (m, 2H); 3.8–3.4 (m, 3H); 2.4–1.5 (m, 8H) ppm. |
|---|---|

EXAMPLE 2

N-[4-(4-Methoxyphenyl)butyryl]-2-S-trifluoroacetylpyrrolidine (a) N-[4-(4-Methoxyphenyl)butyryl]-2-S-(1-hydroxy-2,2,2-trifluoroethyl)pyrrolidine 6 g of trifluoroiodomethane are passed, at 20° C. and while sonicating with ultrasound, into a mixture of 1.38 g of N-[4-(4-methoxyphenyl)butyryl]-S-prolinal and 0.65 g of zinc powder in 15 ml of DMF. After 1 hour, working-up is carried out as described in Example (1a). Chromatography on silica gel using ethyl acetate/cyclohexane (2:1) provides 2 isomers of the title compound in the ratio 2.5:1.

| Isomer 1: $^1$H NMR (CDCl$_3$): $\delta$ = | 7.2–6.6 (m, 4H); 5.5–4.9 (m, 1H); 5.0–4.0 (m, 1H); 3.8 (s, 3H); 3.6–1.6 (m, 10H) ppm. |
|---|---|
| Isomer 2: $^1$H NMR (CDCl$_3$): $\delta$ = | 7.2–6.6 (m, 4H); 6.0–5.5 (m, 1H); 4.6–4.3 (m, 1,H); 3.8 (s, 3H); 4.0–3.2 (m, 2H); |

3.0–1.7 (m, 10H) ppm.

(b) N-[4-(4-Methoxyphenyl)butyryl)]-2-S-trifluoroacetylpyrrolidine

In analogy to the process described in Example (1b), 110 mg of the title compound are obtained as oil from 160 mg of the compound from Example (2a).

$^1$H NMR (CDCl$_3$): δ = 7.2–6.6 (m, 4H); 5.3–4.9 (m, 2H); 4.7–4.2 (m, 1H); 3.8 (s, 3H); 3.6–1.6 (m, 10H) ppm.

We claim:

1. A compound of the formula I

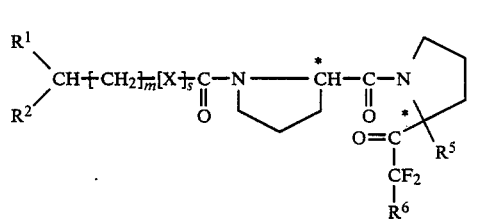

(I)

in which

R$^1$ denotes hydrogen; (C$_1$–C$_6$)-alkyl; or (C$_6$–C$_{12}$)-aryl, said aryl being optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino or a (C$_1$ or C$_2$)-alkylenedioxy;

R$^2$ denotes hydrogen; (C$_1$–C$_6$)-alkyl; (C$_6$–C$_{12}$)-aryl; (C$_6$–C$_{12}$)-aryloxy; (C$_7$–C$_{13}$)-aroyl; hydroxyl or (C$_1$–C$_4$)-alkoxy, each of said aryl, aryloxy and aroyl being optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy; or R$^1$ and R$^2$ together represent benzylidene in which the phenyl ring is optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy;

R$^5$ denotes hydrogen; (C$_1$–C$_6$)-alkyl; (C$_6$–C$_{12}$)-aryl-(C$_1$–C$_5$)-alkyl which is optionally substituted in the aryl moiety by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy;

R$^6$ denotes (C$_1$–C$_8$)-alkyl; (C$_4$–C$_{10}$)-cycloalkyl or (C$_4$–C$_{10}$)-cycloalkyl-(C$_1$–C$_4$)-alkyl, it being possible for one of said cycloalkyl radicals also to contain, dependent on the ring size, up to 4 double-bonds, or to be bridged up to three times, or to contain, dependent on the ring size, up to 4 double-bonds and to be bridged up to three times; (C$_6$–C$_{12}$)-aryl-(C$_1$–C$_5$)-alkyl which is optionally substituted in the aryl moiety by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy; fluorine or a radical C$_q$H$_{(2q+1-r)}$F$_r$ with q = 1, 2, 3, 4 or 5 and r = an integer from 1 to (2q+1);

X denotes oxygen; imino or N-(C$_1$–C$_8$)-alkylimino;

m is 0, 1, 2, 3, 4 or 5; and s is 0 or 1, or a physiologically tolerated salt thereof.

2. A compound of the formula I as claimed in claim 1, in which

R$^1$ denotes hydrogen;

R$^2$ denotes phenyl; phenoxy; benzoyl; each of said phenyl, phenoxy and benzoyl optionally being substituted by one or two identical or different radicals selected from methyl, ethyl, methoxy, fluorine, chlorine, bromine, nitro, hydroxyl, amino, methylamino and dimethylamino, or one methylenedioxy;

R$^5$ denotes hydrogen;

R$^6$ denotes fluorine or perfluoro-(C$_1$–C$_5$)-alkyl;

X denotes oxygen; and m is 0, 1 or 2;

or a physiologically tolerated salt thereof.

3. A compound of the formula I as claimed in claim 1, in which

R$^1$ denotes hydrogen;

R$^2$ denotes phenyl; o-, m- or p-tolyl; o-, m- or p-chlorophenyl; o-, m- or p-fluorophenyl; o-, m- or p-methoxyphenyl; 2,3-, 2,4-, 2,5-, 2,6-, 3,4- or 3,5-dimethoxyphenyl; phenoxy; o-, m- or p-tolyloxy; o-, m- or p-chlorophenoxy; o-, m- or p-fluorophenoxy; o-, m- or p-methoxyphenoxy; 2,3-, 2,4-, 2,5-, 2,6-, 3,4- or 3,5-dimethoxyphenoxy; benzoyl; o-, m- or p-toluoyl; o-, m- or p-chlorobenzoyl; o-, m- or p-fluorobenzoyl; o-, m- or p-methoxybenzoyl; 2,3-, 2,4-, 2,5-, 2,6-, 3,4- or 3,5-dimethoxybenzoyl; hydroxyl or methoxy;

R$^5$ denotes hydrogen;

R$^6$ denotes fluorine or perfluoro-(C$_1$–C$_5$)-alkyl;

X denotes oxygen; and m is 0, 1 or 2;

or a physiologically tolerated salt thereof.

4. A compound of the formula I as claimed in claim 1, in which

R$^2$ denotes hydrogen;

R$^5$ denotes hydrogen;

X denotes oxygen; and m is 1, 2, 3 or 4;

or a physiologically tolerated salt thereof.

5. A compound of the formula I as claimed in claim 1, in which

R$^1$ denotes hydrogen;

R$^2$ denotes phenyl or p-methoxyphenyl;

R$^5$ denotes hydrogen;

R$^6$ denotes fluorine;

X denotes oxygen; and m is 0 or 2;

or a physiologically tolerated salt thereof.

6. A compound of the formula I as claimed in claim 1, in which

R$^1$ denotes hydrogen or (C$_1$–C$_6$)-alkyl;

R$^2$ denotes hydrogen; (C$_6$–C$_{12}$)-aryl; (C$_6$–C$_{12}$)-aryloxy; (C$_7$–C$_{13}$)-aroyl; each of said aryl, aryloxy and aroyl being optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$-alkylamino, or one (C$_1$ or C$_2$)-alkylenedioxy;

R$^5$ denotes hydrogen;

$R^6$ denotes fluorine or a radical $C_qH_{(2q+1-r)}F_r$ with $q=1, 2, 3, 4$ or $5$ and $r=$ an integer from $1$ to $(2q+1)$; and X denotes oxygen;

or a physiologically tolerated salt thereof.

7. The compound of claim 1 which is N-(N-benzyloxycarbonyl-S-prolyl)-2-S-trifluoroacetylpyrrolidine.

8. The compound N-[4-(4-methoxyphenyl)butyryl]-2-S-trifluoroacetylpyrrolidine.

9. A pharmaceutical composition comprising a compound of the formula I or a pharmaceutically tolerated salt thereof as claimed in claim 1 in an amount effective for treating at least one disease of the central nervous system, and a pharmaceutically acceptable carrier.

10. A pharmaceutical composition comprising a compound of the formula I or a pharmaceutically tolerated salt thereof as claimed in claim 1 in an amount effective for treating at least one disease of the central nervous system, wherein said compound or said salt is an inhibitor of prolyl-endopeptidase, and a pharmaceutically acceptable carrier.

11. A method of inhibiting prolyl-endopeptidase by administering a compound of formula I or a pharmaceutically tolerated salt thereof as claimed in claim 1 in an amount effective for treating at least one disease of the central nervous system.

* * * * *